United States Patent [19]

Krämer et al.

[11] Patent Number: 6,001,829

[45] Date of Patent: Dec. 14, 1999

[54] FLUOROPROPENYL OXADIAZOLES AND THE USE THEREOF AS PEST CONTROL AGENTS

[75] Inventors: Wolfgang Krämer, Burscheid; Udo Kraatz, Leverkusen; Wolfram Andersch, Bergisch Gladbach; Christoph Erdelen, Leichlingen; Andreas Turberg, Haan; Norbert Mencke, Leverkusen, all of Germany

[73] Assignee: Bayer Aktiengesellschaft, Leverkusen, Germany

[21] Appl. No.: 09/066,384

[22] PCT Filed: Oct. 24, 1996

[86] PCT No.: PCT/EP96/04663

§ 371 Date: Apr. 29, 1998

§ 102(e) Date: Apr. 29, 1998

[87] PCT Pub. No.: WO97/17335

PCT Pub. Date: May 15, 1997

[30] Foreign Application Priority Data

Nov. 6, 1995 [DE] Germany .......................... 195 41 261

[51] Int. Cl.$^6$ .................................................. A61K 31/535
[52] U.S. Cl. ...................... 514/236.2; 514/361; 514/364; 548/100
[58] Field of Search ................................ 514/236.2, 361, 514/364; 548/100

[56] References Cited

U.S. PATENT DOCUMENTS

| | | | |
|---|---|---|---|
| 4,861,367 | 8/1989 | Nyfeler et al. | 514/252 |
| 4,952,580 | 8/1990 | Martinet et al. | 514/236.2 |

FOREIGN PATENT DOCUMENTS 0 290 379  11/1988  European Pat. Off. .

OTHER PUBLICATIONS

Ando et al., "3–(3,3–Dihal–2–propenyl) . . . and photostability," Journal of Agricultural and Food Chemistry, vol. 31, No. 2 (1983) pp. 250–253.

*Primary Examiner*—Everett White
*Attorney, Agent, or Firm*—Sprung Kramer Schaefer & Briscoe

[57] ABSTRACT

The present invention relates to novel fluoropropenyl heterocycles of the formula (I) found $$CF_2=CX-CH_2-Het \qquad (1),$$

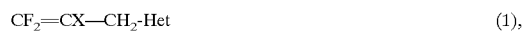

in which

Het, X and R are each as defined in the description, to processes for their preparation and to their use for controlling animal pests.

4 Claims, No Drawings

FLUOROPROPENYL OXADIAZOLES AND THE USE THEREOF AS PEST CONTROL AGENTS

This application is a 371 of PCT/EP96/04663 filed Oct. 24, 1996.

The present invention relates to novel fluoropropenyl heterocycles, to processes for their preparation and to their use for controlling animal pests, in particular insects, arachnids and nematodes, encountered in agriculture, in forests, in the protection of stored products and of materials, and in the hygiene sector.

It is already known that certain fluorobutenyl compounds have nematicidal activity (cf. for example WO 88/00183). However, the efficacy and the activity spectrum of these compounds, in particular at low application rates and concentrations, are not always entirely satisfactory.

This invention, accordingly, provides novel compounds of the formula (I)

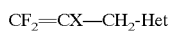  (I), in which
X represents hydrogen or halogen,
Het represents one of the radicals

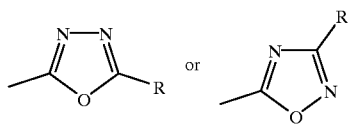

and
R represents respectively optionally substituted alkyl, aryl, aralkyl or hetaryl.

Furthermore, it has been found that the compounds of the formula (I) are obtained when A) amidoximes of the formula (II)

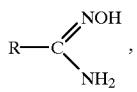  (II)

in which
R is as defined above
are reacted with acyl chlorides of the formula (III)

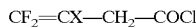  (III), in which
X is as defined above,
if appropriate in the presence of a diluent and if appropriate in the presence of a base, and the resulting intermediates of the formula (IV)

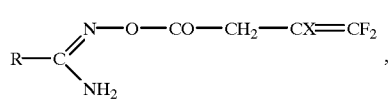  (IV)

in which
R and X are each as defined above
are, if appropriate, isolated and, if appropriate, cyclized in the presence of a base, or
B) carbohydrazides of the formula (V)

  (V), in which
R is as defined above
are reacted with acyl chlorides of the formula (III)

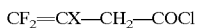  (III), in which
X represents hydrogen or halogen,
in the presence of a diluent and in the presence of a base to give compounds of the formula (VI)

  (VI)

in which
R and X are each as defined above,
and these compounds are, if appropriate, isolated and, if appropriate, cyclized in the presence of a diluent and, if appropriate, in the presence of a dehydrating agent.

Finally, it has been found that the novel compounds of the formula (I) have pronounced biological properties and are suitable especially for controlling animal pests, in particular insects, arachnids and nematodes, encountered in agriculture, in forests, in the protection of stored products and of materials, and in the hygiene sector.

The formula (I) provides a general definition of the compounds according to the invention.

Preferred substituents or ranges of the radicals listed in the formulae mentioned hereinabove and hereinbelow are illustrated below.

X preferably represents hydrogen, fluorine or chlorine.
Het preferably represents one of the radicals or

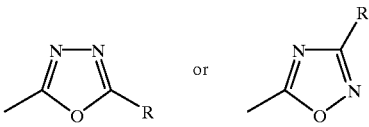

R preferably represents $C_1$–$C_8$-alkyl, $C_1$–$C_8$-halogenylalkyl, $C_1$–$C_8$-alkoxy-$C_1$–$C_8$-alkyl, $C_1$–$C_8$-alkylthio-$C_1$–$C_8$-alkyl, phenoxy-$C_1$–$C_4$-alkyl which is optionally halogen-, $C_1$–$C_6$-alkyl-, $C_1$–$C_6$-alkoxy-, $C_1$–$C_6$-halogenoalkyl- or $C_1$–$C_6$-halogenoalkoxy-substituted in the phenyl moiety, preferably represents optionally halogen-, $C_1$–$C_6$-alkyl-, $C_1$–$C_6$-alkoxy-, $C_1$–$C_6$-alkylthio-, $C_1$–$C_6$-halogenoalkyl-, $C_{1-C_8}$-alkoxycarbonyl-, aminocarbonyl-, $C_1$–$C_6$-alkylaminocarbonyl-, di-$C_1$–$C_6$-alkylaminocarbonyl-, nitro-, cyano- or SCN-substituted phenyl, preferably represents phenyl-$C_1$–$C_4$-alkyl which is optionally halogen-, $C_1$–$C_4$-alkyl, $C_1$–$C_4$-halogenoalkyl-, $C_1$–$C_4$-alkoxy- or $C_1$–$C_4$-alkylthio-substituted in the phenyl moiety, or preferably represents optionally benzo-fused and optionally halogen-, $C_1$–$C_6$-alkyl-, $C_1$–$C_6$-halogenoalkyl- or phenyl- (which is optionally substituted by halogen, $C_1$–$C_6$-alkyl, $C_1$–$C_4$-alkoxy, $C_1$–$C_4$-halogenoalkyl or $C_1$–$C_4$-halogenoalkoxy) substituted 5- or 6-membered heteraryl having one or two hetero atoms from the group consisting of oxygen, sulphur and nitrogen.

X particularly preferably represents hydrogen or fluorine.

Het particularly preferably represents one of the radicals

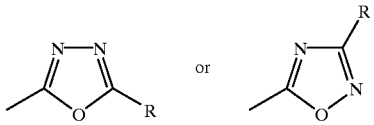

R particularly preferably represents $C_1$–$C_4$-alkyl, $C_1$–$C_3$-halogenoalkyl, $C_1$–$C_4$-alkoxy-$C_1$–$C_4$-alkyl, $C_1$–$C_4$-alkylthio-$C_1$–$C_4$-alkyl, phenoxy-$C_1$–$C_2$-alkyl which is optionally fluorine-, chlorine-, $C_1$–$C_4$-alkyl-, $C_1$–$C_4$-alkoxy-, $C_1$–$C_3$-halogenoalkyl- or $C_1$–$C_3$-halogenoalkoxy-substituted in the phenyl moiety, particularly preferably represents optionally fluorine-, chlorine-, $C_1$–$C_4$-alkyl-, $C_1$–$C_4$-alkoxy-, $C_1$–$C_4$-alkylthio-, nitro- or cyano-substituted phenyl, particularly preferably represents phenyl-$C_1$–$C_2$-alkyl which is optionally fluorine-, chlorine-, $C_1$–$C_4$-alkyl-, or $C_1$–$C_2$-halogenoalkyl-substituted in the phenyl moiety, or particularly preferably represents respectively optionally benzo-fused and optionally fluorine-, chlorine-, $C_1$–$C_4$-alkyl-, $C_1$–$C_2$-halogenoalkyl- or phenyl- (which is optionally substituted by halogen, $C_1$–$C_4$-alkyl, $C_1$–$C_2$-halogenoalkyl, $C_1$–$C_2$-alkoxy or $C_1$–$C_2$-halogenoalkoxy) substituted furanyl, thienyl or pyridyl.

X very particularly preferably represents fluorine.

Het very particularly preferably represents one of the radicals

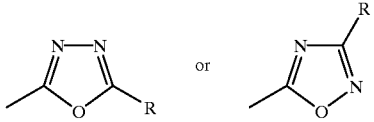

R very particularly preferably represents $C_1$–$C_3$-alkyl, chloromethyl, trifluoromethyl, $C_1$–$C_4$-alkoxymethyl, $C_1$–$C_4$-alkylthiomethyl, phenoxymethyl which is optionally fluorine-, chlorine-, $C_1$–$C_3$-alkyl-, $C_1$–$C_3$-alkoxy-, trifluoromethyl- or trifluoromethoxy-substituted in the phenyl moiety, very particularly preferably represents optionally fluorine-, chlorine-, $C_1$–$C_3$-alkyl-, $C_1$–$C_3$-alkoxy- or $C_1$–$C_3$-alkylthio-substituted phenyl, very particularly preferably represents benzyl which is optionally fluorine-, chlorine-, $C_1$–$C_3$-alkyl- or trifluoromethyl-substituted in the phenyl moiety, or very particularly preferably represents respectively optionally fluorine-, chlorine-, $C_1$–$C_3$-alkyl- or trifluoromethyl- or phenyl- (which is optionally substituted by fluorine, chlorine, $C_1$–$C_3$-alkyl, trifluoromethyl or trifluoromethoxy) substituted furanyl, thienyl or pyridyl.

X most preferably represents fluorine.

Het most preferably represents one of the radicals

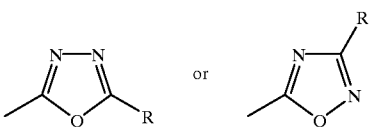

R most preferably represents optionally fluorine-, chlorine-, methyl-, ethyl-, methoxy- or ethoxy-substituted phenyl or most preferably represents optionally fluorine-, chlorine-, methyl- or ethyl-sustituted furanyl, thienyl or pyridyl.

The abovementioned general or preferred radical definitions or illustrations apply to the end products and, correspondingly, to the starting materials and intermediates. These radical definitions can be combined with one another as desired, that is to say combinations between the respective preferred ranges are also possible.

Preference according to the invention is given to those compounds of the formula (I) which contain a combination of the definitions listed above as being preferred (preferable).

Particular preference according to the invention is given to those compounds of the formula (I) which contain a combination of definitions listed above as being particularly preferred.

Very particular preference according to the invention is given to those compounds of the formula (I) which contain a combination of the definitions listed above as being very particularly preferred.

Most particular preference according to the invention is given to those compounds of the formula (I) which contain a combination of the definitions listed above as being most particularly preferred.

In the radical definitions mentioned hereinabove and hereinbelow, hydrocarbon radicals such as alkyl or alkenyl are—including in combination with hetero atoms such as alkoxy or alkylthio—straight-chain or branched as far as this is possible.

Using 4-methylbenzamide oxime and 3,4,4-trifluorobut-3-enoyl chloride as starting materials in the preparation of compounds of formula (I) according to process A), the course of the reaction can be represented by the following equation:

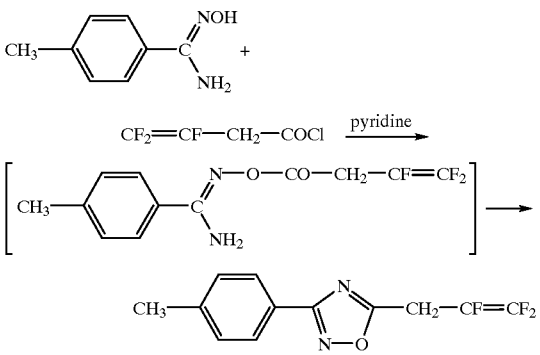

Using 4-chlorobenzhydrazide and 3,4,4-trifluorobut-3-enoyl chloride as starting materials in the preparation of compounds of the formula (I) according to process B), the course of the reaction can be represented by the following equation:

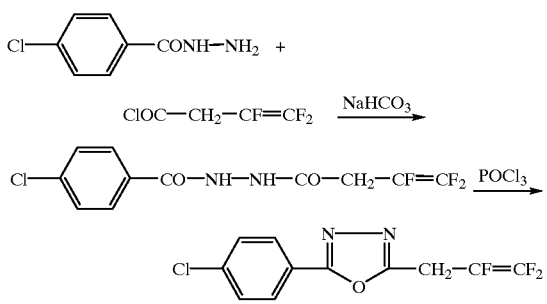

The process A) according to the invention for preparing compounds of the formula (I) is characterized in that initially amidoximes of the formula (II) are reacted with acyl chlorides of the formula (III), if appropriate in the presence of a base.

Diluents which are suitable for this purpose are organic solvents. Examples include hydrocarbons such as cyclohexane, toluene or benzene, halogenated, in particular chlorinated, hydrocarbons such as methylene chloride, chloroform, dichloroethane or chlorobenzene and furthermore nitriles such as acetonitrile.

The reaction of the amidoximes of the formula (II) with the acyl chlorides of the formula (III) is preferably carried out in the presence of a base. Suitable bases are organic bases, in particular tertiary amines such as diazabicycloundecane (DBU), diazabicyclononene (DBN), diazabicyclooctane (DABCO), pyridine or triethyleneamine, and also inorganic bases, in particular alkali metal or alkaline earth metal carbonates, bicarbonates, hydroxides or oxides such as potassium carbonate, sodium bicarbonate, sodium hydroxide or calcium oxide, In general, it is not necessary to isolate the intermediates of the formula (IV). They can be converted into the desired 1,2,4-oxadiazoles for example by prolonged heating and/or in the presence of the abovementioned bases.

The reaction temperature in the process A) according to the invention can be varied within a relatively wide range. In general, the reaction is carried out at temperatures between −10° C. and 180° C., preferably between 0° C. and 140° C.

In general, the starting materials of the formulae (II) and (III) are employed in approximately equimolar amounts, however, it is also possible to use one component or the other in a relatively large excess (up to about 2:1).

In general, at least an equimolar amount of the base is also added.

The process A) according to the invention is generally carried out under atmospheric pressure (cf. Houben-Weyl, Methoden der organischen Chemie, Vol. E 8c, part 3, p. 409 ff).

The process B) according to the invention for preparing compounds of the formula (I) is characterized in that carbohydrazides of the formula (II) are initially reacted with acyl chlorides of the formula (III) in the presence of a diluent and in the presence of a base to give the diacylhydrazines of the formula (VI) (step 1), which are, if appropriate, isolated and, if appropriate, cyclized in the presence of a diluent and, if appropriate, in the presence of a dehydrating agent (step 2).

Diluents which are suitable for step 1 of the process B) according to the invention are organic solvents. Examples include aliphatic or aromatic, optionally halogenated (in particular chlorinated) hydrocarbons such as cyclohexane, toluene, xylene, dichloromethane, trichloromethane, dichloroethane or chlorobenzene, ethers such as tetrahydrofuran or dioxane, nitriles such as acetonitrile, amides such as dimethylformamide or sulphoxides such as dimethyl sulphoxide.

The reaction can also be carried out in a two-phase system consisting of water and an organic solvent such as water/dichloromethane or water/toluene.

Suitable bases for step 1 of the process B) according to the invention are both organic bases, in particular tertiary amines such as DBU, DBN, DABCO, pyridine or triethylamine, and inorganic bases, in particular alkali metal carbonates, bicarbonates or hydroxides such as sodium carbonate, potassium carbonate, sodium bicarbonate or sodium hydroxide.

The intermediates of the formula (VI) can be isolated prior to step 2 (cyclization) of the process B) according to the invention. However, it is also possible to carry out these steps directly after step 1, i.e. without isolation of the intermediates of the formula (VI).

Step 2 of the process B) according to the invention (cf. Houben-Weyl, Methoden der org. Chemie, Vol. E 8c, part 3, p. 563 ff) is preferably carried out in the presence of a diluent. Suitable diluents are inert organic solvents, for example optionally halogenated (chlorinated) hydrocarbons such as toluene, xylene or dichlorobenzene or amides such as dimethylacetamide.

Step 2 of the process B) according to the invention is carried out in the presence of a dehydrating agent. Suitable dehydrating agents are the customary dehydrating agents. Examples include phosphorus oxychloride, polyphosphoric acid, p-toluenesulphonic acid and phosphorus pentoxide.

It may be advantageous to carry out the reaction in an apparatus comprising a water separator.

The reaction temperature in the process B) according to the invention can be varied within a relatively wide range. In general, the reaction is carried out at temperatures between 0° C. and 200° C., preferably between 20° C. and 150° C.

The temperature at which step 1 is carried out may differ from the temperature at which step 2 is carried out (cf. Preparation Examples).

In general, the starting materials of the formula (III) and (V) are employed in approximately equimolar amounts, however, it is also possible to employ one component or the other in a relatively large excess (up to 3:1, preferably up to 1.5:1).

In general, at least an equimolar amount of base is also added.

The process B) according to the invention is generally carried out under atmospheric pressure.

The intermediates of the formula (VI) can also be prepared by reacting carbohydrazides of the formula (VII)

$$CF_2=CX—CH_2—CO—NH—NH_2 \qquad (VII)$$

in which

X is as defined above with acyl chlorides of the formula (VIII)

$$R—COCl \qquad (VIII)$$

in which

R is as defined above.

This reaction can be carried out under the reaction conditions described above under step 1 of the process B) according to the invention.

The amidoximes of the formula (II) required as starting materials and the carbohydrazides of the formula (V) are known and/or can be prepared by generally known methods (see for example Houben-Weyl, Methoden der organischen Chemie. Vol. (VIII), p. 676; F. Eloy, R. Lenaers, Chem. Rev. 62, 155 (1962)).

The acyl chlorides of the formula (III) furthermore required as starting materials are known (see for example U.S. Pat. No. 5,389,680 and EP 0 432 861).

The active compounds are suitable for controlling animal pests, in particular insects, arachnids and nematodes, encountered in agriculture, in forests, in the protection of stored products and of materials, and in the hygiene sector. They can preferably be employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and Scutigera spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*.

From the order of the Dermaptera, for example, *Forficula auricularia*.

From the order of the Isoptera, for example, Reticulitermes spp.

From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., *Trichoplusia ni, Carpocapsa pomonella*, Pieris spp., Chilo spp., *Pyrausta nubilalis, Ephestia kuehniella, Galleria mellonella. Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp. and Trichodorus spp.

The compounds of the formula (I) according to the invention in particular have outstanding nematicidal activity, for example against *Meloidogyne incognita*. They have good folar insecticidal action.

The active compounds according to the invention act systemically.

The active compounds can be converted to the customary formulations, such as solutions, emulsions, wettable powders, suspensions, powders, dusting agents, pastes, soluble powders, granules, suspo-emulsion concentrates, natural and synthetic materials impregnated with active compound and very fine capsules in polymeric substances.

These formulations are produced in a known manner, for example by mixing the active compounds with extenders, that is liquid solvents and/or solid carriers, if appropriate with the use of surfactants, that is emulsifiers and/or dispersants and/or foam-formers.

In the case of the use of water as an extender, organic solvents can, for example, also be used as auxiliary solvents. Essentially, the following are suitable liquid solvents: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Possible further additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms, prepared from these formulations. as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino [alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cypro-conazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furan-carboxylic acid, oxytetracycline, probenazole, streptomycin, tecloftalam, copper sulphate and other copper preparations.

Insecticides/Acaiicides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichiofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyradaphenthion, pyresmethrin, pyrethrum, pyridaben, pyrimidifen, pyriproxyfen, quinalphos, RH 5992, salithion, sebufos, silafluofen, sulfotep, suiprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichiorfon, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compounds according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene and stored-product pests, the active compound has excellent residual action on wood and clay and good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example. hamsters, guinea-pigs, rats and mice. By controlling these arthropods, it is intended to reduce mortality and decreased performances (in meat, milk, wool, hides, eggs, honey and the like), so that more economical and simpler animal keeping is possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, directly or after dilution by a factor of 100 to 10 000, or they may be used in the form of a chemical bath.

The preparation and the use of the active compounds according to the invention are illustrated by the examples below.

PREPARATION EXAMPLES

Example 1

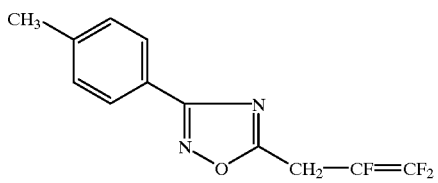

At 20° C., 6.0 g (38 mmol) of 3,4,4-trifluorobutenoyl chloride are added dropwise to a solution of 6.0 g (40 mmol) of 4-methylbenzamide oxime in 60 ml of dioxane and 4.9 g (62 mmol) of pyridine, and the mixture is subsequently stirred at 90° C. for 12 h. The mixture is then poured into water, the product is extracted with methylene chloride and the organic phase is concentrated under reduced pressure.

The crude product thus obtained is chromatographed over silica gel using the system chloroform/ethyl acetate =4:1. 5.5 g (57% yield of theory) of crystalline 3-(4-methylphenyl)-5-(2,3,3-trifluoroprop-2-enyl)-1,2,4-oxadiazole of mp. 46–50° C. are obtained.

Example 2

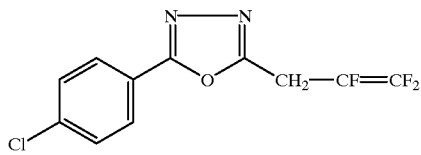

4.0 g (13.7 mmol) of 1-(4-chlorobenzoyl)-2-(3,3,4-trifluoro-but-3-enoyl)-hydrazine in 50 ml of toluene are heated under reflux with 4.2 g (27.4 mmol) of phosphorus oxychloride for 1 h. The toluene is subsequently removed under reduced pressure and the residue is taken up in methylene chloride/ice-water. The organic phase is concentrated under reduced pressure and purified by silica gel column chromatography using the system chloroform/ethyl acetate (9:1). 2.3 g (64.5% yield of theory) of 2-(4-chlorophenyl)-5-(2,3,3-trifluoroprop-2-enyl)-1,3-4-oxadiazole of mp. 72° C. are obtained.

Prepartion of the Starting Materials

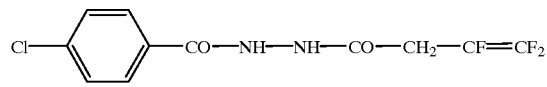

5.2 g (30.3 mmol) of 4-chlorobenzhydrazide in 50 ml of dichloromethane are admixed with a solution of 2.8 g (33 mmol) of sodium bicarbonate in 25 ml of water, and 4.8 g (30.3 mmol) of 3,4,4-trifluorobut-3-enoyl chloride are subsequently added with stirring at 0° C. After stirring overnight, the precipitated 1-(4-chlorobenzoyl)-2-(3,4,4-trifluorobut-3-enoyl)-hydrazine is filtered off with suction.

Yield: 8.0 g (90.4% of theory) of mp. 198° C.

Similar to Examples 1 and 2 and/or according to the general preparation procedures, the compounds of the formula (I) listed in the table below were obtained.

| Ex. No. | Formula | Physic. Data |
|---|---|---|
| 3 | ![compound 3: 2,6-dichlorophenyl oxadiazole with CH₂—CF=CF₂] | log p* = 3.44 (pH 2) |
| 4 | ![compound 4: CH₂Cl substituted oxadiazole with CH₂—CF=CF₂] | log p = 2.08 |
| 5 | ![compound 5: 2-chlorophenyl oxadiazole with CH₂—CF=CF₂] | log p = 3.30 (pH 2) |

-continued

| Ex. No. | Formula | Physic. Data |
|---|---|---|
| 6 | 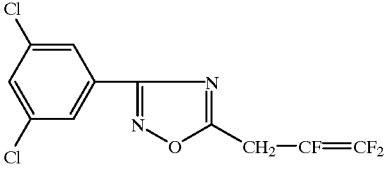 | log p = 4.72 (pH 2) |
| 7 | 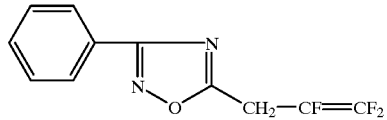 | log p = 3.20 (pH 2) |
| 8 | 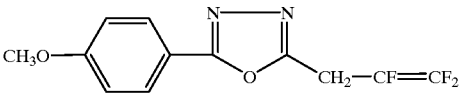 | log p = 2.46 (pH 7.5) |
| 9 | 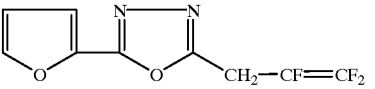 | log. p = 1.89 (pH 7.5) $n_D^{20}$ = 1.4980 |
| 10 | 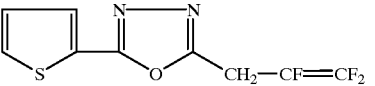 | log p = 2.19 (pH 7.5) $n_D^{20}$ = 1.5304 |

*log p: logarithm to base ten of the n-octanol/water partition coefficient, determined by reverse phase HPLC analysis using $H_2O/CH_3CN$.

Use Example

Example A

Critical Concentration Test/Nematodes

| Test nematode: | Meloidogyne incognita |
|---|---|
| Solvent: | 4 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The active compound preparation is intimately mixed with soil which is heavily infested with the test nematodes. The active compound concentration in the preparation is immaterial, only the amount of active compound per unit volume of soil, which is given in ppm (=mg/l), matters. The treated soil is transferred into pots, lettuce seeds are sown, and the pots are kept at a greenhouse temperature of 25° C.

After four weeks, the lettuce roots are checked for infestation with nematodes (root galls) and the efficacy of the active compound in % is determined. The efficacy is 100% when infestation is avoided completely and 0% when the infestation level is just as high as in the control plants in untreated, but equally infested, soil.

In this test, an efficacy of 100% was shown, for example, by the compound of Preparation Example 10, at an exemplary active compound concentration of 20 ppm.

Example B

Phaedon Larvae Test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and are populated with mustard beetle larvae (*Phaedon cochleariae*) while the leaves are still moist.

After the desired period of time, the kill in % is determined. 100% means that all the beetle larvae have been killed, 0% means that none of the beetle larvae have been killed.

In this test, a kill of 100% is shown, after 7 days, for example, by the compounds of Preparation Examples 1, 2 and 7, at an exemplary active compound concentration of 0.1%.

Example C

Plutella Test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and are populated with caterpillars of the diamond back moth (*Plutella xylostella*) while the leaves are still moist.

After the desired period of time, the kill in % is determined. 100% means that all the caterpillars have been killed, 0% means that none of the caterpillars have been killed.

In this test, a kill of at least 90% was shown, after 7 days, for example, by the compounds of Preparation Examples 1, 2, 3, 5, 7 and 8, at an exemplary active compound concentration of 0.1%.

Example D

Spodoptera Test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the active compound preparation of the desired concentration and are populated with caterpillars of the owlet moth *Spodoptera frugiperda* while the leaves are still moist.

After the desired period of time, the kill in % is determined. 100% means that all the caterpillars have been killed, 0% means that none of the caterpillars have been killed.

In this test, a kill of at least 85% was shown, after 7 days, for example, by the compounds of Preparation Examples 1, 3 and 7, at an exemplary active compound concentration of 0.1%.

Example E

Nephotettix Test

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Rice seedlings (*Oryzae sativa*) are treated by being dipped into the active compound preparation of the desired concentration and are populated with larvae of the green rice leaf hopper (*Nephotettix cincticeps*) while the seedlings are still moist.

After the desired period of time, the kill in % is determined. 100% means that all the leaf hoppers have been killed; 0% means that none of the leaf hoppers have been killed.

In this test, a kill of 100% was shown, after 6 days, for example, by the compounds of Preparation Examples 1, 2 and 3, at an exemplary active compound concentration of 0.1%.

Example F

Myzus Test (Duration of Activity after Spraying)

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Bean shoots (*Vicia faba*) which are heavily infested by the black bean aphid (*Aphis fabae*) are treated by being dipped into the active compound preparation of the desired concentration.

After the desired period of time, the kill in % is determined. 100% means that all aphids have been killed, 0% means that none of the aphids have been killed.

In this test, a kill of 90% and 80% was shown, for example, by the compounds of Preparation Examples 1, and 2, respectively, at an exemplary active compound concentration of 0.1%.

Example G

Test with Fly Larvae/Development-Inhibitory Action

| Test animals: | all larval stages of Lucilia cuprina (OP resistent) [pupae and adults (without contact with the active compound)] |
|---|---|
| Solvent: | 35 parts by weight of ethylene glycol monomethyl ether |
| | 35 parts by weight of nonylphenol polyglycol ether |

To produce a suitable preparation, 3 parts by weight of the active compound are mixed with 7 parts by weight of the abovementioned solvent-emulsifier mixture, and the resulting emulsion concentrate is diluted with water to the concentration desired in each case.

For each concentration, 30 to 50 larvae are introduced into a test tube which contains horse meat (1 cm$^3$). 500 µl of the dilution to be tested are pipetted onto this horse meat. The test tubes are placed in plastic beakers whose bottom is covered with sea sand, and kept in an air-conditioned room (26° C.±1.5° C., 70%±10% relative humidity). The activity is examined (larvicidal action) after 24 hours and 48 hours. After emergence of the larvae (about 72 h), the test tubes are removed and perforated plastic lids are fitted onto the beakers. After 1.5 times the development time (hatching of control flies), the hatched flies and the pupae/cocoons are counted.

The activity criterion is the incidence of death in the treated larvae after 48 h (larvicidal effect), or the inhibition of hatching of adults from pupae or the inhibition of pupae formation. The criterion for the in vitro activity of a substance is the inhibition of the development of the fleas, or a development standstill before the adult stage. 100% larvicidal action means that all the larvae have been killed after 48 hours. 100% development-inhibitory action means that no adult flies have hatched.

In this test, an activity of 100% was shown, for example, by the compounds of Preparation Examples 3, 5 and 7, at an exemplary active compound concentration of 1000 ppm.

Example H

Test with Boophilus Microplus Resistent/SP-Resistent Parkhurst Strain

| | |
|---|---|
| Test animals: | Adult females which have sucked themselves full |
| Solvent: | Dimethyl sulphoxide |

20 mg of active compound are dissolved in 1 ml of dimethyl sulphoxide, and lower concentrations are prepared by diluting in the same solvent.

The test is carried out in 5 replications. I μl of the solutions is injected into the abdomen, and the animals are transferred into dishes and kept in an air-conditioned room. The activity is determined via the inhibition of oviposition. 100% means that no tick has deposited eggs.

In this test, an activity of 100% was shown, for example, by the compound of Preparation Example 1, at an exemplary active compound concentration of 200 μg/animal.

We claim:

1. A compound of the formula (I)

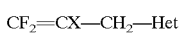   (I), in which
X represents hydrogen or halogen,
Het represents one of the radicals

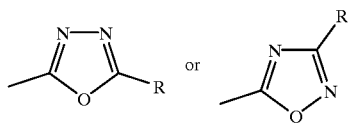

and
R represents respectively optionally substituted alkyl, aryl, aralkyl or heteroaryl.

2. A process for preparing the compound of the formula (I) according to claim 1, wherein
A) amidoximes of the formula (II)

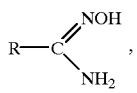   (II)

in which
R is as defined in claim 1
are reacted with acyl chlorides of the formula (III)

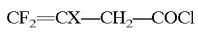   (III), in which
X is as defined in claim 1,
optionally in the presence of a diluent and optionally in the presence of a base, and the resulting intermediates of the formula (IV)

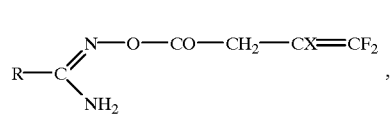   (IV)

in which
R and X are each as defined above
are optionally isolated and cyclized in the presence of a base, or B) carbohydrazides of the formula (V)

   (V), in which
R is as defined above
are reacted with acyl chlorides of the formula (III)

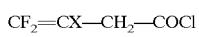   (III), in which
X represents hydrogen or halogen,
in the presence of a diluent and in the presence of a base to give compounds of the formula (VI)

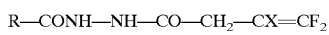   (VI)

in which
R and X are each as defined above,
and these compounds are optionally isolated and cyclized in the presence of a diluent and optionally in the presence of a dehydrating agent.

3. A pesticidal composition comprising at least one compound of the formula (I) according to claim 1 and an extender.

4. A method of combating unwanted pests which comprises administering to such pests or to a locus from which it is desired to exclude such pests a pesticidally effective amount of a compound according to claim 1.

* * * * *